(12) United States Patent
Baturin (10) Patent No.: US 10,578,563 B2
(45) Date of Patent: Mar. 3, 2020

(54) PHASE CONTRAST IMAGING COMPUTED TOMOGRAPHY SCANNER

(71) Applicant: Carestream Health, Inc., Rochester, NY (US)

(72) Inventor: Pavlo Baturin, Rochester, NY (US)

(73) Assignee: Carestream Health, Inc., Rochester, NY (US)

(*) Notice: Subject to any disclaimer, the term of this patent is extended or adjusted under 35 U.S.C. 154(b) by 207 days.

(21) Appl. No.: 15/352,655

(22) Filed: Nov. 16, 2016

(65) Prior Publication Data

US 2017/0146467 A1 May 25, 2017

Related U.S. Application Data

(60) Provisional application No. 62/257,277, filed on Nov. 19, 2015.

(51) Int. Cl.
| | |
|---|---|
| *G01N 23/00* | (2006.01) |
| *G01N 23/046* | (2018.01) |
| *G01N 23/04* | (2018.01) |
| *A61B 6/00* | (2006.01) |
| *A61B 6/06* | (2006.01) |
| *A61B 6/03* | (2006.01) |
| *A61B 6/02* | (2006.01) |

(52) U.S. Cl.
CPC ......... *G01N 23/046* (2013.01); *A61B 6/4291* (2013.01); *A61B 6/484* (2013.01); *G01N 23/04* (2013.01); *A61B 6/027* (2013.01); *A61B 6/032* (2013.01); *A61B 6/06* (2013.01); *A61B 6/4035* (2013.01); *G01N 2223/401* (2013.01); *G21K 2207/005* (2013.01)

(58) Field of Classification Search
CPC ..... A61B 6/4035; A61B 6/4291; A61B 6/484; A61B 6/027
See application file for complete search history.

(56) References Cited

U.S. PATENT DOCUMENTS

| | | | |
|---|---|---|---|
| 5,812,629 | A | 9/1998 | Clauser |
| 6,560,309 | B1 | 5/2003 | Becker et al. |
| 7,346,204 | B2 | 3/2008 | Ito |
| 7,453,981 | B2 | 11/2008 | Baumann et al. |
| 7,639,786 | B2 | 12/2009 | Baumann et al. |

(Continued)

FOREIGN PATENT DOCUMENTS

| | | |
|---|---|---|
| CN | 101011256 | 8/2007 |
| CN | 101036582 | 9/2007 |

(Continued)

OTHER PUBLICATIONS

International Search Report, International application No. PCT/US2016/062389, dated Feb. 2, 2017, 2 pages.

(Continued)

*Primary Examiner* — Dani Fox (57) ABSTRACT

A grating based differential phase contrast imaging (DPCI) apparatus and acquisition technique whereby the system generates horizontal moiré fringes on a detector of the DPCI system by tilting at least one of the G1 and G2 gratings, and capturing images of an object including moving the object in a direction perpendicular to the lines of the moiré fringes.

14 Claims, 5 Drawing Sheets

(56) References Cited

U.S. PATENT DOCUMENTS

| | | | |
|---|---|---|---|
| 7,646,843 B2 | 1/2010 | Popescu et al. | |
| 7,693,256 B2 | 4/2010 | Brahme et al. | |
| 7,817,777 B2 | 10/2010 | Baumann et al. | |
| 8,280,000 B2 | 10/2012 | Takahashi | |
| 8,515,002 B2 | 8/2013 | Huang et al. | |
| 8,855,395 B2 | 10/2014 | Baturin et al. | |
| 9,001,867 B2 | 4/2015 | Baturin et al. | |
| 9,001,967 B2 | 4/2015 | Baturin et al. | |
| 9,357,975 B2 | 6/2016 | Baturin et al. | |
| 9,494,534 B2 | 11/2016 | Baturin et al. | |
| 9,700,267 B2 | 7/2017 | Baturin et al. | |
| 9,724,063 B2 | 8/2017 | Baturin et al. | |
| 9,795,350 B2 | 10/2017 | Baturin et al. | |
| 9,907,524 B2 | 3/2018 | Baturin et al. | |
| 10,058,300 B2 | 8/2018 | Baturin et al. | |
| 10,096,098 B2 | 10/2018 | Baturin et al. | |
| 2005/0249328 A1 | 11/2005 | Bruder et al. | |
| 2007/0183560 A1 | 8/2007 | Popescu et al. | |
| 2007/0183582 A1 | 8/2007 | Baumann et al. | |
| 2007/0183583 A1 | 8/2007 | Baumann et al. | |
| 2008/0009717 A1 | 1/2008 | Herrmann et al. | |
| 2008/0014643 A1 | 1/2008 | Bjorkholm | |
| 2008/0075228 A1 | 3/2008 | Tasaki | |
| 2008/0123805 A1 | 5/2008 | Zellerhoff | |
| 2008/0273653 A1 | 11/2008 | Niwa et al. | |
| 2009/0092227 A1 | 4/2009 | David et al. | |
| 2009/0097730 A1 | 4/2009 | Kasai et al. | |
| 2009/0116720 A1 | 5/2009 | Ritman | |
| 2009/0128830 A1 | 5/2009 | Kottler et al. | |
| 2010/0220832 A1 | 9/2010 | Ning et al. | |
| 2010/0220834 A1 | 9/2010 | Heismann et al. | |
| 2010/0246764 A1 | 9/2010 | Itoh et al. | |
| 2010/0246765 A1 | 9/2010 | Murakoshi et al. | |
| 2010/0272230 A1 | 10/2010 | Koehler | |
| 2010/0272235 A1 | 10/2010 | Takahashi | |
| 2011/0085639 A1 | 4/2011 | Nakamura et al. | |
| 2011/0135057 A1 | 6/2011 | Mori et al. | |
| 2011/0206181 A1 | 8/2011 | Linev | |
| 2011/0243302 A1 | 10/2011 | Murakoshi | |
| 2011/0243305 A1 | 10/2011 | Tada | |
| 2012/0020461 A1 | 1/2012 | Roessl et al. | |
| 2012/0045108 A1 | 2/2012 | Shechter | |
| 2012/0057677 A1 | 3/2012 | Vogtmeier et al. | |
| 2012/0093284 A1 | 4/2012 | Takemoto et al. | |
| 2012/0114098 A1 | 5/2012 | Mikami et al. | |
| 2012/0163554 A1 | 6/2012 | Tada | |
| 2012/0250972 A1* | 10/2012 | Tada | A61B 6/4291 382/132 |
| 2013/0010926 A1 | 1/2013 | Tada | |
| 2013/0028378 A1 | 1/2013 | Stutman et al. | |
| 2013/0034209 A1 | 2/2013 | Ouchi | |
| 2013/0108015 A1 | 5/2013 | Kottler et al. | |
| 2013/0156284 A1 | 6/2013 | Koehler et al. | |
| 2013/0259194 A1 | 10/2013 | Yip et al. | |
| 2013/0308750 A1 | 11/2013 | Ishii | |
| 2014/0044234 A1 | 2/2014 | Hashimoto et al. | |
| 2014/0177789 A1 | 6/2014 | Baturin et al. | |
| 2014/0185746 A1 | 7/2014 | Baturin et al. | |
| 2014/0185896 A1 | 7/2014 | Baturin et al. | |
| 2014/0226782 A1 | 8/2014 | Stutman et al. | |
| 2014/0226783 A1 | 8/2014 | Ning et al. | |
| 2014/0226785 A1 | 8/2014 | Stutman et al. | |
| 2014/0270060 A1 | 9/2014 | Date et al. | |
| 2014/0270061 A1 | 9/2014 | Yamaguchi | |
| 2014/0286477 A1 | 9/2014 | Ishii et al. | |
| 2014/0341347 A1 | 11/2014 | Radicke | |
| 2014/0355740 A1 | 12/2014 | Koehiler et al. | |
| 2015/0092916 A1 | 4/2015 | Baturin et al. | |
| 2015/0110247 A1 | 4/2015 | Baturin et al. | |
| 2015/0117599 A1 | 4/2015 | Yun et al. | |
| 2015/0131777 A1 | 5/2015 | Makifuchi et al. | |
| 2015/0182178 A1 | 7/2015 | Baturin et al. | |
| 2015/0187096 A1 | 7/2015 | Baturin et al. | |
| 2015/0216499 A1 | 8/2015 | Martens et al. | |
| 2016/0038107 A1 | 2/2016 | Baturin et al. | |
| 2016/0095562 A1 | 4/2016 | Baturin et al. | |
| 2016/0125599 A1 | 5/2016 | Stampanoni et al. | |
| 2016/0242714 A1 | 8/2016 | Baturin et al. | |
| 2016/0317109 A1 | 11/2016 | Yip et al. | |
| 2017/0035378 A1 | 2/2017 | Baturin et al. | |
| 2017/0082559 A1* | 3/2017 | Arboleda | A61B 6/484 |
| 2017/0146467 A1 | 5/2017 | Baturin | |

FOREIGN PATENT DOCUMENTS

| | | |
|---|---|---|
| CN | 101257851 | 9/2008 |
| CN | 101952900 | 1/2011 |
| CN | 102197303 | 9/2011 |
| CN | 102325498 | 1/2012 |
| CN | 102639059 | 8/2012 |
| CN | 102740775 | 10/2012 |
| CN | 102802529 | 11/2012 |
| CN | 104132953 | 11/2014 |
| CN | 104244832 | 12/2014 |
| DE | 102006015356 | 8/2007 |
| EP | 1731099 | 12/2006 |
| JP | 2007-203074 | 8/2007 |
| JP | 2009-150875 | 7/2009 |
| JP | 2011-504395 | 2/2011 |
| JP | 2011-078669 | 4/2011 |
| JP | 2012-090945 | 5/2012 |
| JP | 2012-125343 | 7/2012 |
| JP | 2013-138836 | 7/2013 |
| JP | 2013-536723 | 9/2013 |
| JP | 2013-255536 | 12/2013 |
| JP | 2012-005820 | 4/2014 |
| JP | 2015-519091 | 7/2015 |
| JP | 2016-501630 | 1/2016 |
| TW | 201424695 | 7/2014 |
| WO | 2011/122715 | 10/2011 |
| WO | 2012/029048 | 3/2012 |
| WO | 2012/080125 | 6/2012 |
| WO | 2013/126296 | 8/2013 |
| WO | 2013/148010 | 10/2013 |
| WO | 2013/187150 | 12/2013 |
| WO | 2014/100063 | 6/2014 |
| WO | 2014/137318 | 9/2014 |
| WO | 2015/102756 | 7/2015 |
| WO | 2015/102757 | 7/2015 |
| WO | 2017/087586 | 5/2017 |

OTHER PUBLICATIONS

Jian Fu et al., Helical differential X-Ray phase-contrast computed tomography, Physica Medica, vol. 30, pp. 374-379, 2014.
Thomas Thuring, et al., Non-linear regularized phase retrieval for unidirectional X-ray differential phase contrast radiography, Optics Express, vol. 19, Issue 25, pp. 25545-25558, Optical Society of America 2011, issn: 10944087.
Supplementary European Search Report, dated Nov. 27, 2015, European Application No. 13769560.7, 2 pages.
H.N. Cardinal and A. Fenster "An accurate method for direct dual-energy calibration and decomposition" Medical Physics, 1990, May-Jun. vol. 17, No. 3, pp. 327-341.
Chapman, D., Thomlinson, et al., "Diffraction enhanced x-ray imaging," Phys. Med. Biol., 42, 2015, (1997).
Bonse, et al., "An x-ray interferometer," Appl. Phys. Lett. 6(8), 155-156, (1965).
Ingal. V. N., et al., "X-ray plane-wave topography observation of the phase contrast from noncrystalline object," J. PhD 28(11), 2314-2317, (1995).
Wilkins, S. W., et al., "Phase-contrast imaging using polychromatic hard X-rays," Nature (London) 384(6607) 335-338, (1996).
Momose, A., et al., "Demonstration of X-ray Talbot interferometry," Jpn. J. Appl. Phys. 42, L866-L868, (2003).
Wietkamp, T., et al., "X-ray phase imaging with a grating interferometer," Opt. Exp. 13(16), 6296-6304, (2006).
Pfeiffer, F., "Phase retrieval and differential phase-contrast imaging with low-brilliance X-ray sources", Nature Phys. 2, 258-261, (2006).
International Search Report, International application No. PCT/US2014/066027, dated May 2, 2015, 2 pages.

(56) References Cited

OTHER PUBLICATIONS

International Search Report, International application No. PCT/US2014/066033, dated Apr. 28, 2015, 2 pages.
International Search Report, International application No. PCT/US2013/026301, dated Jun. 3, 2013, 3 pages.
International Search Report, International application No. PCT/US2013/075898, dated Apr. 22, 2014, 2 pages.
Thomas Thuring, Compact X-ray grating interferometry for phase and dark-field computed tomography in the diagnostic energy range, Swiss Federal Institute of Technology Zurich, 2013, pp. 1-180.
C. Kottler et al., Grating interferometer based scanning setup for hardy-ray phase contrast imaging, Review of Scientific Instruments, vol. 78, 034710, 2007, pp. 1-4.
Christian Kottler et al., "Dual energy phase contrast x-ray with Talbot-Lau interferometer," Journal of Applied Physics, 2010, 108, pp. 114906-1-114906-6.
Commonly assigned U.S. Appl. No. 61/939,925, entitled: Method and Apparatus for Fabrication and Tuning of Grating-Based Differential Phase Contrast Imaging System filed Feb. 14, 2014, by Baturin et al.
Commonly assigned U.S. Appl. No. 14/143,183, entitled: Phase Retrieval From Differential Phase Contrast Imaging filed Dec. 30, 2013, by Baturin et al.
Commonly assigned U.S. Appl. No. 61/892,490, entitled: Surrogate Phantom for Differential Phase Contrast Imaging filed Oct. 18, 2013, by Baturin et al.
Commonly assigned U.S. Appl. No. 14/143,254, entitled: Large FOV Phase Contrast Imaging Based on Detuned Configuration Including Acquisition and Reconstruction Techniques filed Dec. 30, 2013, by Baturin et al.
Chinese Search Report, dated Mar. 30, 2017, Chinese Application No. 201380067294.3 3 pages.

* cited by examiner

PHASE CONTRAST IMAGING COMPUTED TOMOGRAPHY SCANNER

CROSS REFERENCE TO RELATED APPLICATIONS

This application claims priority to U.S. Patent Application Ser. No. 62/257,277, filed Nov. 19, 2015, in the name of Baturin, and entitled DETUNED PHASE CONTRAST IMAGING HELICAL COMPUTED TOMOGRAPHY SCANNER.

This application is related in certain respects to U.S. patent application Ser. No. 14/874,748, filed Oct. 5, 2015, in the name of Baturin et al., and entitled MATERIAL DECOMPOSITION TECHNIQUE USING X-RAY PHASE CONTRAST IMAGING SYSTEM; U.S. patent application Ser. No. 14/621,823, filed Feb. 13, 2015, in the name of Baturin et al., and entitled METHOD AND APPARATUS FOR FABRICATION AND TUNING OF GRATING-BASED DIFFERENTIAL PHASE CONTRAST IMAGING SYSTEM; U.S. patent application Ser. No. 14/143,183, filed Dec. 30, 2013, in the name of Baturin et al., and entitled PHASE RETRIEVAL FROM DIFFERENTIAL PHASE CONTRAST IMAGING; U.S. Pat. No. 9,494,534, issued Nov. 15, 2016, in the name of Baturin et al., and entitled MATERIAL DIFFERENTIATION WITH PHASE CONTRAST IMAGING; U.S. patent application Ser. No. 14/517,072, filed Oct. 17, 2014, in the name of Baturin et al., and entitled SURROGATE PHANTOM FOR DIFFERENTIAL PHASE CONTRAST IMAGING; U.S. Pat. No. 9,357,975, issued Jun. 7, 2016, in the name of Baturin et al., and entitled LARGE FOV PHASE CONTRAST IMAGING BASED ON DETUNED CONFIGURATION INCLUDING ACQUISITION AND RECONSTRUCTION TECHNIQUES; U.S. Pat. No. 8,855,395, issued Oct. 7, 2014, in the name of Baturin et al., and entitled CONDITIONAL LIKELIHOOD MATERIAL DECOMPOSITION AND METHODS OF USING THE SAME; U.S. Pat. No. 9,001,967, issued Apr. 7, 2015, in the name of Baturin et al., and entitled SPECTRAL GRATING-BASED DIFFERENTIAL PHASE CONTRAST SYSTEM FOR MEDICAL RADIOGRAPHIC IMAGING; U.S. patent application Ser. No. 13/724,096, filed Dec. 21, 2012, in the name of Baturin et al., and entitled GRATING-BASED DIFFERENTIAL PHASE CONTRAST IMAGING SYSTEM WITH ADJUSTABLE CAPTURE TECHNIQUE FOR MEDICAL RADIOGRAPHIC IMAGING; and U.S. patent application Ser. No. 13/724,037, filed Dec. 21, 2012, in the name of Yip et al., and entitled HYBRID SLOT-SCANNING GRATING-BASED DIFFERENTIAL PHASE CONTRAST IMAGING SYSTEM FOR MEDICAL RADIOGRAPHIC IMAGING; all ten of which are incorporated herein by reference in their entirety.

BACKGROUND OF THE INVENTION

The subject matter disclosed herein relates to phase contrast imaging systems and methods.

BRIEF DESCRIPTION OF THE INVENTION

Figure 7:
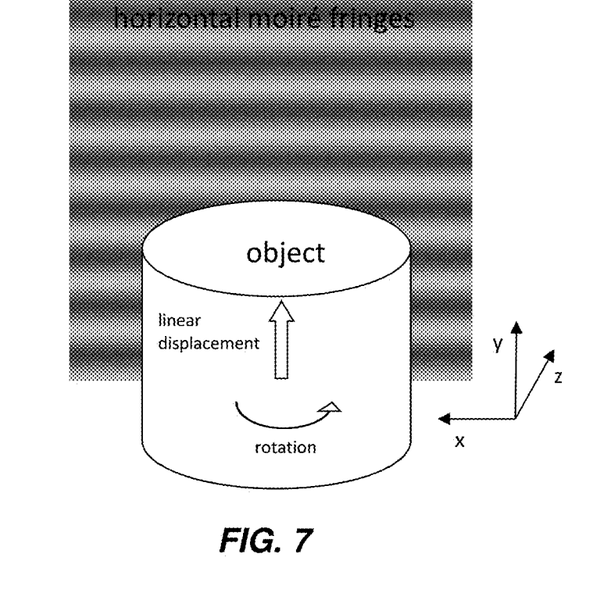
FIG. 7 is a schematic diagram of relative motion of the object across the moiré pattern for a helical CT configuration.

An embodiment of the methods and apparatuses disclosed in this patent application includes an exemplary helical CT scan system that may be implemented in a slot scanning PCI configuration. The PCI system may be set to operate in a detuned mode wherein a horizontal moiré pattern (relative to a vertical orientation of the system's grating bars) may be modulated in the plane of the detector. The PCI scan of the object would take advantage of a non-phase-stepping technique, e.g., continuous motion, whereby the gratings' relative positions in the PCI system 100 would be fixed and the object would be continuously moved across the moiré fringes, or the object would be fixed and the moiré fringes would be continuously moved across the object. In one embodiment, this system allows moving the object in a helical CT fashion, i.e., a simultaneous linear translation across the moiré fringes and a rotation (FIG. 7). In addition, tipping or tilting of the absorption grating G2, relative to a z-direction x-ray beam path (FIG. 10B) may also be implemented for the purpose of: decreasing the fraction of incoherent radiation passed through the G2 grating bars and tuning the PCI system to higher x-ray energies.

Figure 1:
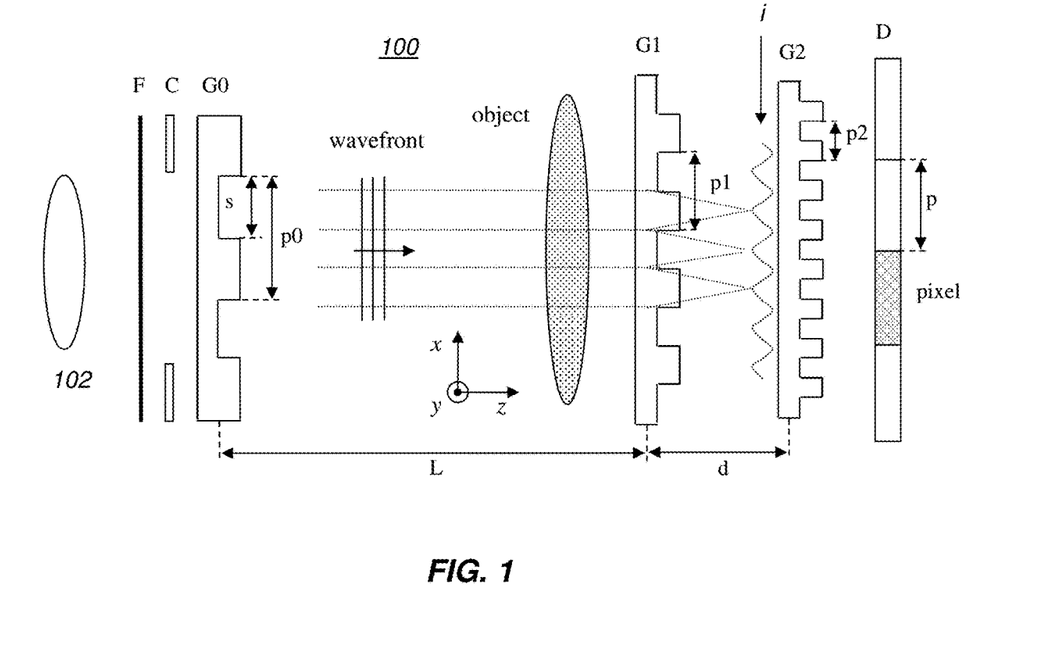
FIG. 1 illustrates a three-grating Talbot-Lau phase contrast imaging setup.

In one current embodiment, a grating based DPCI technology may be utilized. One schematic of a three-grating DPCI system is shown in FIG. 1. Here, the DPCI system comprises three gratings: 1) a source absorption grating G0; 2) a phase grating G1; and 3) an absorption grating G2. The working principles of a DPCI system invoke Talbot-Lau interference phenomena. Namely, the G0 grating serves as a multi-slit source of coherent x-ray radiation. Each slit s of the G0 grating may be considered as an independent source of radiation that, at a certain distance, produces an x-ray beam of sufficient coherence to establish interferometric effects at downstream gratings and detectable at a detector. In the case of a two-grating DPCI system, the G0 grating may be replaced with a coherent x-ray source or an array of coherent x-ray sources. The interference between x-rays is generated by the phase grating G1. It produces a repetitive wave-like interference pattern at the G2 phase grating that duplicates a shape of the G1 grating at certain distances, e.g., d, known as Talbot distances. When the x-ray beam, or wave, passes through an object to be imaged positioned in front or behind phase grating G1, the generated interference pattern contains information about the wave's phase shifts and diffractions caused by physical features in or on the object. The interference pattern is then modulated onto the x-ray imager, or digital radiographic detector D having a two-dimensional array of photosensitive elements, using the absorption grating G2.

A grating based differential phase contrast imaging (DPCI) apparatus and acquisition technique is disclosed whereby the system generates horizontal moiré fringes on a detector of the DPCI system by tilting at least one of the G1 and G2 gratings, and capturing images of an object including moving the object in a direction perpendicular to the lines of the moiré fringes.

The grating based DPCI apparatus and acquisition technique may also be used for producing a helical computed tomography (CT) scan. A helical CT scan can be invoked when a DPCI system is set to produce a non-zero frequency moiré pattern. The relative displacement of the scanned object and moiré pattern may be used to acquire a continuous motion scan. The DPCI system that employs such an acquisition technique can be implemented in both large field of view (FOV) and slot scanning configurations.

In one embodiment, a method includes providing a DPCI system having an x-ray source, a G1 grating, a G2 grating, and a digital detector. Horizontal moiré fringes are generated on the detector by tilting at least one of the G1 and G2 gratings of the system relative to each other prior to capturing images of an object placed in the system.

In one embodiment, a method includes providing a DPCI system having an x-ray source, a G1 grating, a G2 grating, and a digital detector. Moiré fringes are generated on the detector on the detector, including tilting the G1 grating prior to capturing images of an object placed in the system.

In one embodiment, a method includes providing a DPCI system having an x-ray source, a G1 grating, a G2 grating, and a digital detector. Moiré fringes are generated on the detector, including tilting the G2 grating toward the detector, and not tilting the G1 grating, prior to capturing images of an object placed in the system.

In one embodiment, a method includes providing a DPCI system having an x-ray source, a G1 grating, a G2 grating, and a digital detector. Moiré fringes are generated on the detector, including tilting the G1 grating toward the detector, and not tilting the G2 grating, prior to capturing images of an object placed in the system.

In one embodiment, a method includes providing a DPCI system having an x-ray source, a G1 grating, a G2 grating, and a digital detector. Moiré fringes are generated on the detector, including tilting the G1 grating away from the detector, and not tilting the G2 grating, prior to capturing images of an object placed in the system.

In one embodiment, a method includes providing a DPCI system having an x-ray source, a G1 grating, a G2 grating, and a digital detector. Moiré fringes are generated on the detector, including tilting the G2 grating away from the detector, and not tilting the G1 grating, prior to capturing images of an object placed in the system.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

The methods and apparatuses disclosed herein include exemplary differential phase contrast imaging systems which, in one or more embodiments, may be implemented in a slot scanning configuration. The exemplary phase contrast imaging systems may also be set to operate in a detuned mode wherein a horizontal moiré pattern, which is perpendicular to an orientation of the grating bars, may be modulated in the plane of the detector. The object scan would take advantage of a non-phase-stepping technique whereby the gratings' positions would be fixed and the object to be scanned would be moved across (perpendicular to) the moiré fringes during a scan, or whereby the object is fixed and the moiré fringes are moved across the scanned object. This configuration may allow moving the object in a helical CT fashion, i.e., simultaneous linear translation and rotation. In addition, tipping or tilting of the grating may be performed for the purpose of: i) decreasing a fraction of the incoherent radiation passed through the grating bars and ii) tuning the PCI system to higher x-ray energies.

In one embodiment a grating based differential phase contrast imaging (DPCI) technology may be used. In particular, a two-grating or three-grating DPCI system may be invoked. The schematic of a three-grating DPCI system 100 is shown in FIG. 1. Here, the DPCI system 100 includes three gratings: a source absorption grating G0, a phase grating G1, and an absorption grating G2. The working principles of the DPCI system 100 includes use of Talbot-Lau interference phenomena. Namely, the G0 grating provides a multi-slit source of coherent x-ray radiation after emission of the x-rays from the x-ray source focal spot 102. A filter F and collimator C may also be provided in the DPCI system 100. Each slit s of the G0 grating can be considered as an independent source of radiation that, at a certain distance, produces x-rays having coherence sufficient to establish interferometric effects downstream therefrom. In the embodiment of a two-grating DPCI system, the G0 grating may be replaced with a coherent x-ray source implemented as either a single coherent source or an array of coherent sources. At least part of the interferometric effects are generated by the phase grating G1, which produces a repetitive interference pattern i that duplicates, in certain respects, a shape of the G1 grating at certain distances, e.g., d, known as Talbot distances. When the x-ray wave, or wavefront, is passed through an object to be imaged, positioned in front or behind phase grating G1, the generated interference pattern i contains information about the x-ray wave's phase shifts and diffractions caused by passing through physical features of the object. The interference pattern is then modulated onto the x-ray imager, or digital radiographic detector D, using the absorption grating G2.

To implement a continuous motion of the relatively fixed G1 and G2 gratings, such as using a swing arm as disclosed in U.S. Pat. No. 9,001,967, identified above, the PCI system may be detuned by a predetermined magnitude. In one detuned embodiment, a DPCI system generates a non-zero frequency moiré pattern in the plane of detector, which is immediately adjacent to the absorption grating G2 as shown in FIG. 1. One method to detune the PCI system includes creating an inequality as between the period (or frequency) of the interference pattern i ($p_{int}$) generated by the G1 grating and the period p2 of the absorption grating (FIG. 4B). As a first approximation, an image signal $I_D$ measured by the detector D may be expressed as a multiplication of periodic functions (e.g., cosine) that represent the interference pattern and grating G2:

$$I_D = MTF(f') \otimes [\cos(2\pi f x) \cdot \cos(2\pi g x)] = MTF(f') \otimes [\cos(2\pi(f+g)x) + \cos(2\pi(f-g)x)]/2 \quad (1)$$

Here $f=1/p_{int}$ and $g=1/p2$ are the frequencies of the interference pattern ($p_{int}$) and G2 grating (p2), respectively. MTF is a modulation transfer function and x is a dimension specified in FIG. 1. Due to the micron sizes of both the interference pattern and G2, the f+g summation term produces a periodic function with frequency of approximately 1000 cyc/mm, which virtually cannot be detected. The f'=f−g term is measured by the detector. According to equation (1) if f=g the detected signal is a maximum. The DPCI system in such a case is perfectly tuned. If f≠g, the DPCI system is detuned. In such a case the detector measures a moiré pattern with frequency f'=f−g. These statements and equation (1) hold true with the assumption that the gratings are perfectly aligned, meaning that there is no relative tip and/or tilt present (i.e., the planes of G1 and G2 and their grating bars, respectively, are perfectly parallel to each other). When the relative tilt between G1 and G2 is present (FIG. 8), the equation (1) can be generalized to another form:

$$I_D = MTF(f') \otimes I_0 \cdot \Gamma_{1,2} \cdot (\cos(2\pi f_x x + 2\pi f_y y) \cdot \cos(2\pi g_x x + 2\pi g_y y)) = \quad (2)$$

$$MTF(f') \otimes I_0 \cdot \Gamma_{1,2} \cdot \frac{(\cos(2\pi(f_x - g_x)x + 2\pi(f_y - g_y)y) + \cos(2\pi(f_y + g_y)y))}{2}$$

Figure 2:
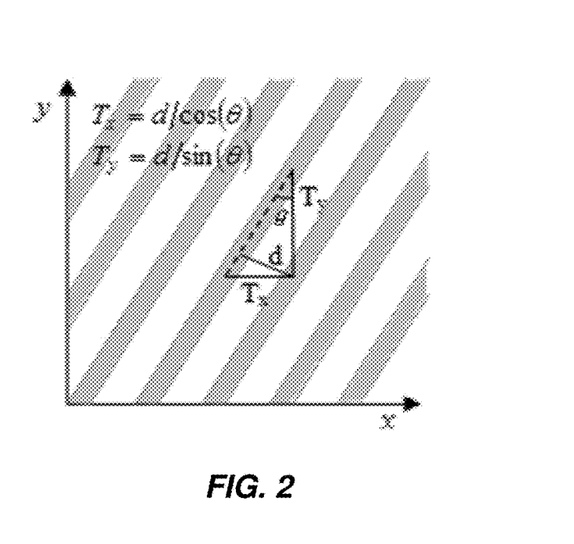
FIG. 2 shows terms defining a tilt angle between gratings G1 and G2.
Figure 3A:
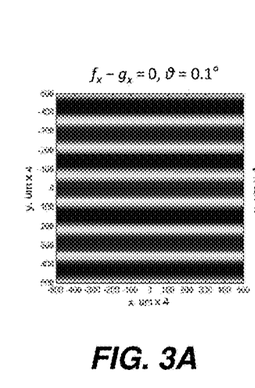
FIGS. 3A-3D show moiré patterns in the plane of the detector for grating tilt angles θ=0.1° and 0.2° and for $f_x - g_x = 0$ cyc/mm, and $f_x - g_x = 1$ cyc/mm.
Figure 3B:
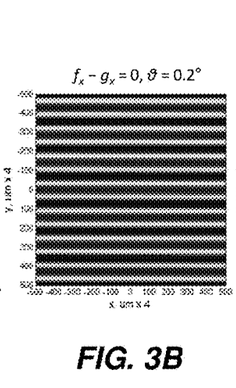
Figure 3C:
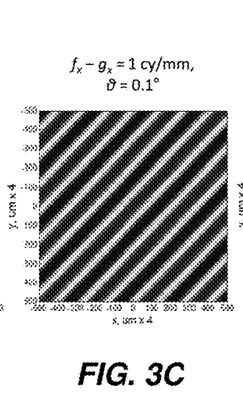
Figure 3D:
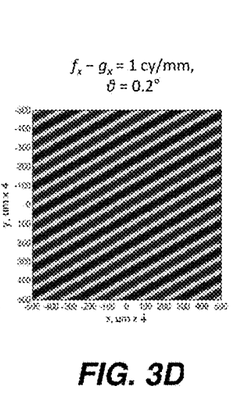

Here, $f_x = \cos(\theta)/d$ and $f_y = \sin(\theta)/d$ are the interference pattern frequencies in the x and y direction, respectively, and $g_{x,y}$ are the frequencies of G2, see FIG. 2. The x-ray detector modulation transfer function, MTF, is evaluated at measured frequency $f' = 1/(T'_y \sin(a \tan(T'_x/T'_y)))$ with periods $T'_x = 1/(f_x - g_x)$ and $T'_y = 1/(f_y - g_y)$. The $I_0$ is the intensity of the x-ray beam incident on $G_1$ grating, and $\Gamma_{1,2}$ is the average transmission intensity through $G_1$ and $G_2$. In FIG. 1 we assume the y-axis in xyz coordinate system to be aligned with the direction of the grating bars in both G1 and G2.

With the tilt present in the DPCI system the moiré pattern modulated by G2 onto detector D would have frequency f' and angle α relative to a vertical y-axis.

$$\alpha = \tan^{-1}((f_y - g_y)/(f_x - g_x)) \quad (3)$$

Figure 5A:
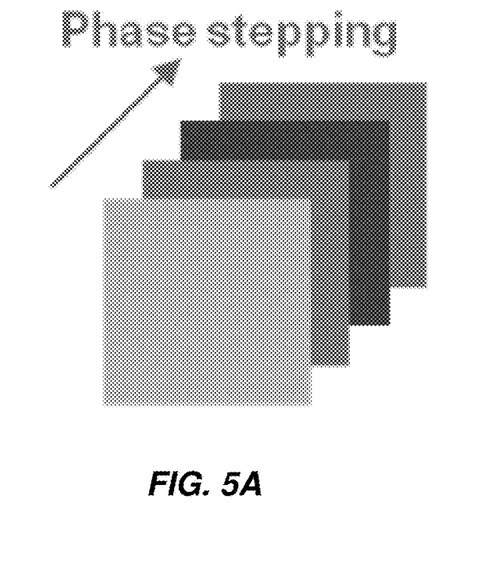
FIGS. 5A-5B show an image sequence created as a result of a phase stepping technique for tuned (5A) and detuned (5B) configurations.

As described earlier (in the rationale of equation (1)), the DPCI system with perfect frequency match ($f_x = g_x$) and gratings alignment ($\theta = 0°$) would produce a zero moiré frequency pattern (FIG. 5A). Tilting of one of the gratings ($\theta \neq 0°$) would result in horizontally oriented moiré fringes (FIG. 7). When frequencies $f_x$ and $g_x$ are not equal (i.e., $f_x \neq g_x$), the moiré pattern with frequency f' and angle α between fringes and vertical axis y is expected. The moiré patterns produced at two different tilt angles $\theta = 0.1°$ and $\theta = 0.2°$ are shown in FIGS. 3A-3D: for $f_x = g_x$ in FIGS. 3A-3B and for $f_x - g_x = 1$ cyc/mm in FIGS. 3C-3D.

Figure 4A:
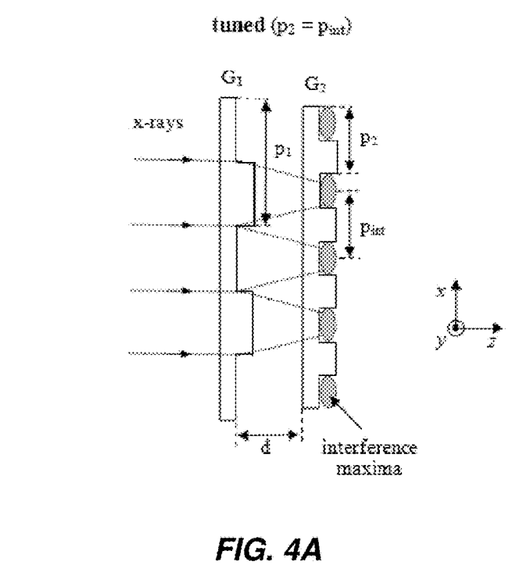
FIGS. 4A-4B show formation of interference patterns for tuned and detuned DPCI configurations.
Figure 4B:
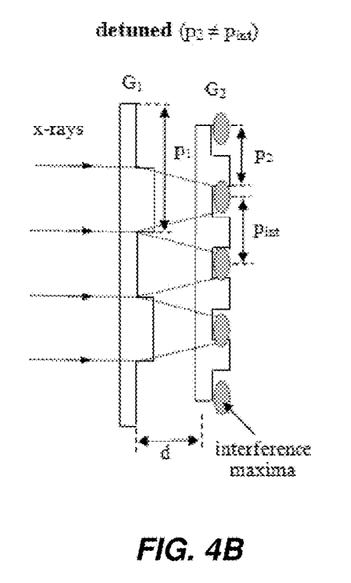
Figure 5B:
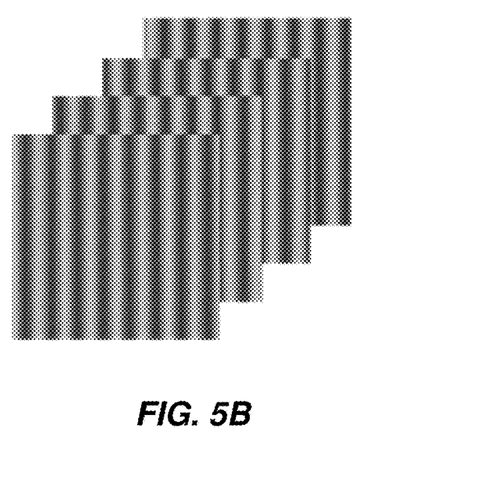
Figure 6:
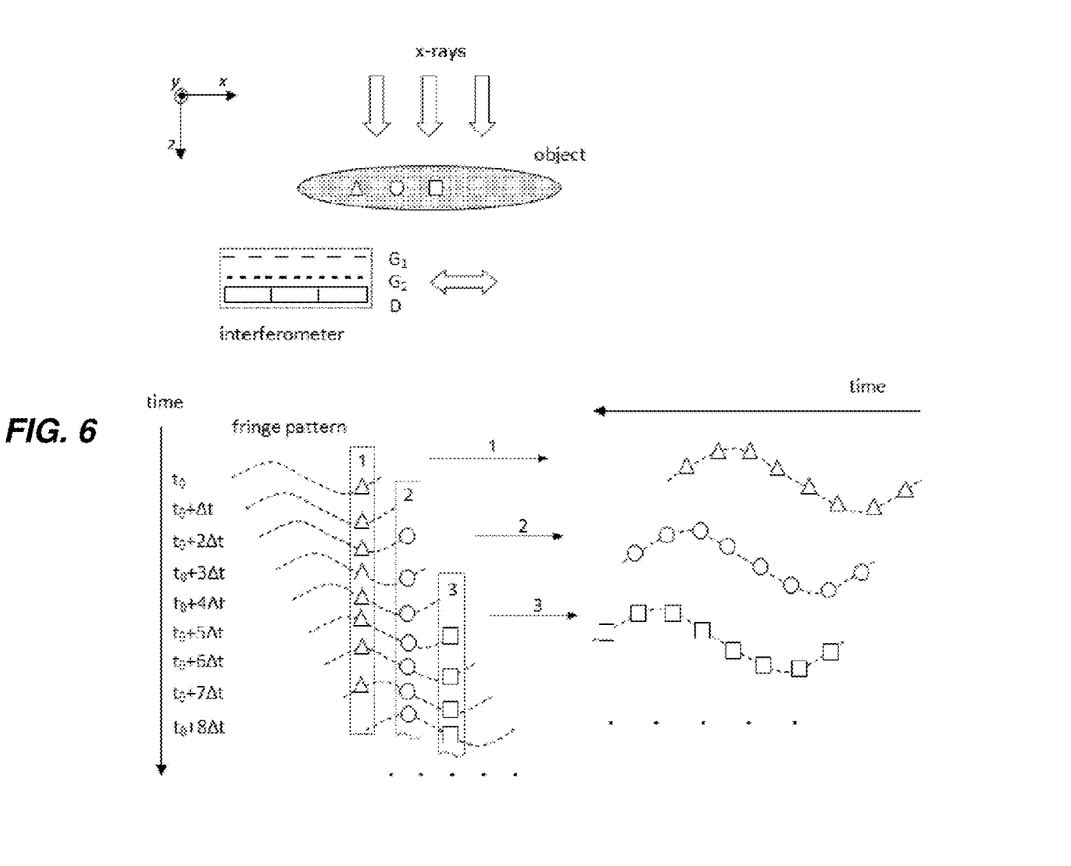
FIG. 6 is a schematic diagram of relative motion of the object across the moiré pattern.

The formation of an interference pattern is schematically shown in FIGS. 4A-4B. The shaded ovals in FIGS. 4A-4B represent local maxima of the interference pattern. When the phase stepping acquisition technique is invoked, such as described in U.S. Pat. No. 9,001,967 identified above, the G2 grating steps over the shaded ovals and modulates signals onto the digital detector. The resulting images for a 4-step acquisition are shown in FIGS. 5A-5B. FIG. 5A represents figures obtained using a perfectly tuned configuration while FIG. 5B shows figures obtained using a detuned configuration. In the case of a detuned configuration the moiré fringes move from frame-to-frame by a fraction of its frequency (in the illustrated case by ⅕ cycle/period in each step). When the object is scanned, the moiré pattern moves from frame-to-frame while the object is fixed. Similar behavior can be achieved by fixing the grating (i.e., not stepping them) and moving object relative to the moiré fringes. A schematic illustration of relative object motion (or stepping) across the moiré pattern is shown in FIG. 6, and is described in more detail in U.S. Pat. Nos. 9,001,967 and 9,357,975 identified above.

Figure 10A:
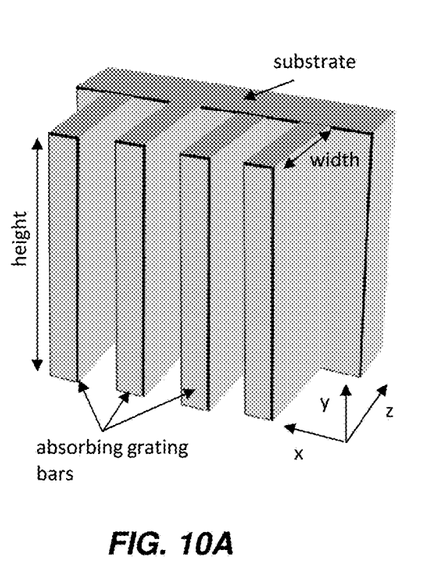
FIGS. 10A-10B are schematic diagrams of an absorption grating and its tilting along the z-axis.

As shown in FIG. 6 different areas of the object to be imaged will project at different parts of a moiré periodic pattern (for example, cosine). The example of FIG. 6 shows only one period of a moiré fringe produced in the interferometer. At different instances of time, the same area of the object may be projected at different parts of the cosine wave or function. The captured image data then can be rearranged such that each part of the object image is represented by a sine or cosine wave (or so called periodic intensity wave) necessary for DPCI image reconstruction. To make acquisition and reconstruction successful, this type of relative motion may be perpendicular to the length, or height, orientation of the grating bars (FIG. 10A). For example, if the grating bars are oriented in y-dimension (FIG. 10A) then the relative motion may occur along (parallel to) the x-dimension. Such a configuration is excellent for a slot scanning system; however, it may have a certain drawback when utilized for a CT setup.

In one embodiment, CT motion can be realized by a step and repeat sequence. Namely, the step and repeat procedure may be realized in the following way: 1) the object and moiré fringe are linearly displaced relative to each other by fixing one or the other and moving the remaining one; 2) the object, or moiré fringe, whichever is moved, is then returned to its initial position, and then 3) the object is rotated a predetermined amount and the steps are repeated until a whole CT scan is performed. One shortcoming here may be that the object rotation is performed around the axis parallel to the direction of the fringe pattern, and the proper acquisition requires the relative object-fringe displacement to be perpendicular to the axis of rotation. Such step and repeat CT acquisition may not be optimal.

In one embodiment, a potential CT imaging procedure may include object rotation without relative object-fringe linear displacement. Although it may be feasible, primarily in the case of small angle rotation of the object significantly larger than the period of moiré fringe, the rotation of the object may create a distorted projection onto the moiré fringes as it would do during the linear object-fringe displacement only. A possible shortcoming of this geometry is that it may become impractical for a simultaneous slot scanning CT implementation. In one embodiment, the mechanism could include a multi-pass slot scanning CT, where the slot DPCI assembly passes across the object (perpendicular to grating bars), thereby creating one projection for a whole object and then pass again across the object after it's rotated by a desired angle. Such multiple passes may be performed until a desired number of object rotations is completed.

Thus, one embodiment, which may provide an alternative to the step-and-repeat type of motion disclosed herein, may include:

1) Creating a moiré pattern with horizontally oriented fringes, by relative tilting between G1 and G2 gratings.

2) Moving the object across the horizontal fringe lines. This motion may be described as two independent motions: i) linear displacement to cover one period of moiré fringes and ii) rotation around the object's axis of CT rotation. The linear displacement and rotational motions may be performed simultaneously, which makes it equivalent to a helical CT scan.

FIG. 7 schematically illustrates these disclosed embodiments, showing the designed vertical linear displacement and rotation relative to a horizontal fringe pattern. One advantage of the proposed embodiments is that the DPCI imaging system may be configured in the form of a slot scanning system such as disclosed in U.S. Pat. No. 9,001, 967, identified above. The y-dimension (slot width) can be set small, so the length-wise orientation of the slot would be parallel to the x-dimension. It may be advantageous to keep at least one moiré fringe over a y-dimension field-of-view (FOV) of the DPCI assembly.

Figure 8:
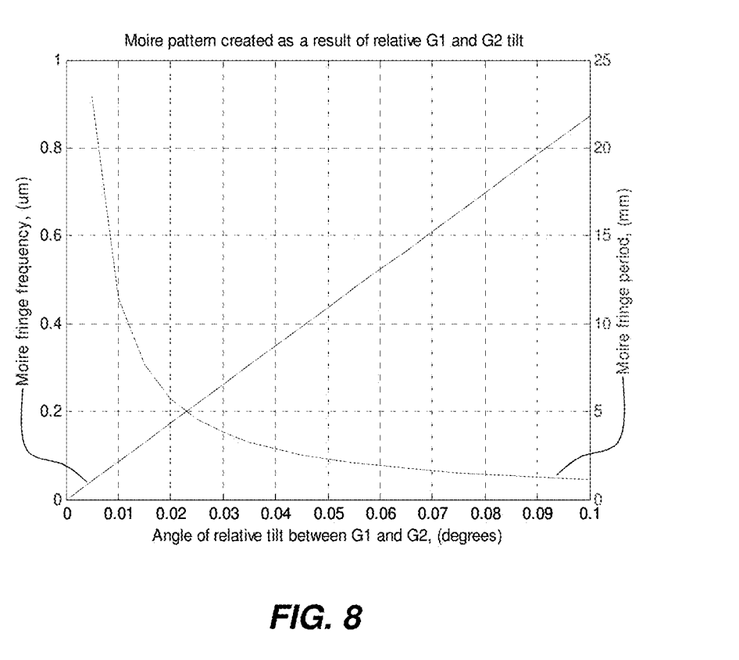
FIG. 8 shows frequency (left y axis) and period (right y axis) of a horizontal moiré pattern created as a result of a relative tilt angle between G1 and G2 gratings (x axis)
Figure 9:
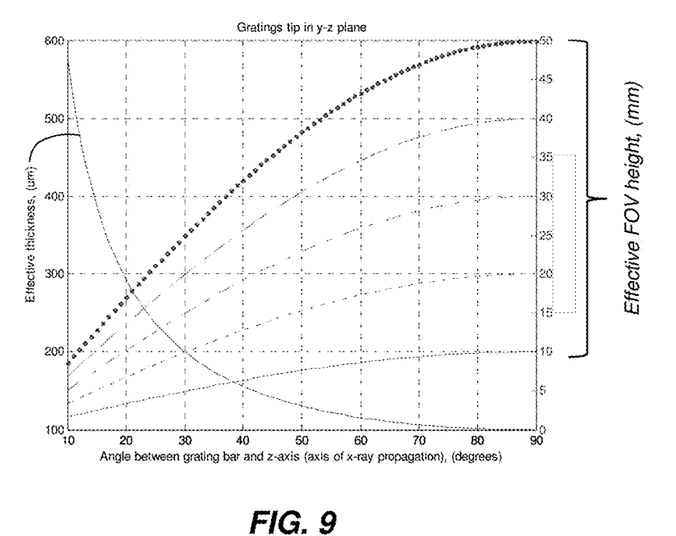
FIG. 9 shows the effect of grating tilting angle (x-axis) in a y-z plane on effective geometrical dimensions (thickness, left y-axis and FOV height, right y-axis) of the grating.
Figure 10B:
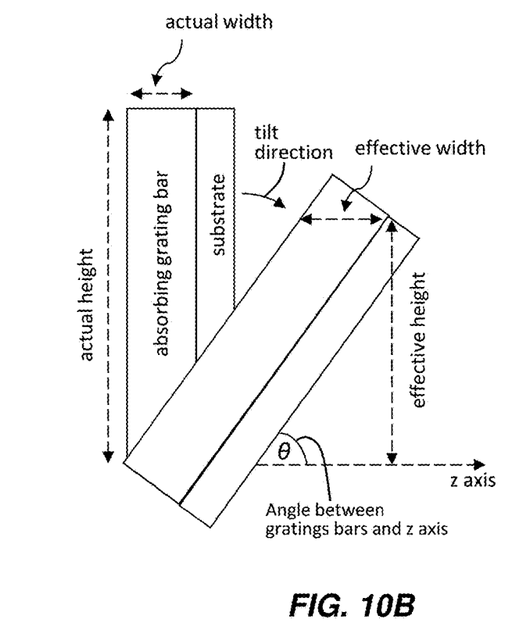

FIG. 8 shows a frequency and period of a modulated moiré pattern as functions of relative tilt between G1 and G2 gratings. The axes of FIG. 8 are demarcated as follows: x axis shows increasing angle of relative tilt between gratings G1 and G2, in degrees; the left vertical axis represents the moiré fringe frequency, in μm (substantially linear plot); the right vertical axis represents the moiré fringe period, in mm (curved plot). It may be desirable to keep the frequency of the modulated moiré pattern low because the detector's modulation transfer function (MTF) is typically higher at lower frequency. The planes of the grating bars may be set parallel to a z-axis direction of the x-rays (FIG. 10A). To increase the effective path length of x-ray propagation through the grating bars, the gratings structure may be tilted, or tipped, towards the z-axis (FIG. 10B). Such tipping would increase effective attenuation of the x-rays through the grating bars, due to the increased effective width, and also would reduce the effective height of the gratings, i.e., it will reduce FOV in the y-dimension. FIG. 9 shows the dependence of these geometrical properties on the angle θ between the gratings bars and the z-axis (as defined in FIG. 10B). The axes of FIG. 9 are demarcated as follows: x axis shows increasing angle between grating bars and z-axis (axis of x-ray propagation), in degrees; the left vertical axis represents effective thickness (or width) in μm (decreasing toward the right plot); the right vertical axis represents the effective FOV height, in mm (decreasing toward the left plots). In other words, this geometrical configuration provides an effective height (which defines FOV in y-dimension) and effective width. The right side axis in FIG. 9 shows the change of effective height, decreasing toward the left, wherein the 90° position means that there is no tilt and actual height=effective height, for different actual heights of the gratings (e.g., 10, 20, 30, 40 and 50 mm). The 100 μm minimum width for the grating was chosen as an example. The width could be smaller (depending on the pitch and duty cycle of the grating).

If we assume, from FIG. 8, that we want to operate at 0.02 degrees of G1 and G2 relative tilt, we can see that one period of horizontal moiré pattern would be stretch to about 5.73 mm. If we want to have two moiré fringes over the y-dimension of FOV we should have the effective height of the grating to be not less than about 12 mm. This means that if the gratings are not tipped along the z-axis then an actual height of the gratings should be at least about 12 mm. If tipping is planned, the actual height of gratings should be more. For example, if an actual 20 mm high grating is tipped by 45 degrees, it will have an effective height of about 14.07 mm, and an effective width of a 100 μm wide absorption grating bar will become about 141.1 μm.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method comprising:
    providing a DPCI system having an x-ray source and, in order along a z axis starting from the x-ray source, a G0 grating, a G1 grating, a G2 grating, and a digital detector;
    aligning in parallel to a y axis, grating bars of the G0 grating, the G1 grating, and the G2 grating; and
    generating moiré fringes on the detector, the moiré fringes aligned in a direction transverse to the y axis, including tilting about an x axis at least one of the G1 and G2 gratings of the system relative to each other,
    wherein the x axis, the y axis and the z axis are perpendicular to each other.

2. The method of claim 1, further comprising capturing images of an object positioned between the x-ray source and the G1 grating, including linearly translating the object in a direction parallel to the y axis.

3. The method of claim 2, further comprising rotating the object about a rotation axis parallel to the y axis, the rotation axis coinciding with the object, to generate a helical scan of the object.

4. The method of claim 3, further comprising using a slot scanning configuration of the DPCI system, wherein a length of each captured image is at least six times greater than its width.

5. A method comprising:
    providing a DPCI system having an x-ray source and, in order along a z axis starting from the x-ray source, a G0 grating, a G1 grating, a G2 grating, and a digital detector;
    aligning in parallel to a y axis, the grating bars of the G0 grating, the G1 grating, and the G2 grating; and
    generating moiré fringes on the detector of the DPCI system, including tilting the G1 grating about an x axis,
    wherein the x axis, the y axis and the z axis are perpendicular to each other.

6. The method of claim 5, further comprising capturing images of an object positioned between the x-ray source and the G1 grating.

7. The method of claim 6, further comprising linearly translating the object in a direction parallel to the y axis during the step of capturing images of the object.

8. The method of claim 7, further comprising rotating the object about a rotation axis parallel to the y axis, the rotation axis coinciding with the object, during the step of capturing images of the object.

9. The method of claim 8, further comprising using a slot scanning configuration of the DPCI system, wherein a length of each captured image is at least six times greater than its width.

10. A method comprising:
    providing a DPCI system having an x-ray source and, in order along a z axis starting from the x-ray source, a G0 grating, a G1 grating, a G2 grating, and a digital detector;
    aligning in parallel to a y axis, grating bars of the G0 grating, the G1 grating, and the G2 grating; and
    generating moiré fringes on the detector of the DPCI system, including tilting the G2 grating about an x axis and not tilting the G1 grating,
    wherein the x axis, the y axis and the z axis are perpendicular to each other.

11. The method of claim 10, further comprising capturing images of an object positioned between the x-ray source and the G1 grating.

12. The method of claim 11, further comprising linearly translating the object in a direction parallel to the y axis during the step of capturing images of the object.

13. The method of claim 12, further comprising rotating the object about a rotation axis parallel to the y axis, the rotation axis coinciding with the object, during the step of capturing images of the object.

14. The method of claim 13, further comprising using a slot scanning configuration of the DPCI system, wherein a length of each captured image is at least six times greater than its width.

* * * * *

UNITED STATES PATENT AND TRADEMARK OFFICE
CERTIFICATE OF CORRECTION

PATENT NO. : 10,578,563 B2  
APPLICATION NO. : 15/352655  
DATED : March 3, 2020  
INVENTOR(S) : Pavlo Baturin Page 1 of 1

It is certified that error appears in the above-identified patent and that said Letters Patent is hereby corrected as shown below:

In the Specification

Column 5, Lines 40-42     Please replace "frequency f'=1/T'$_y$ sin(a tan(T'$_x$/T'$_y$))) with periods T'$_x$=1/(f$_x$-g$_x$) and T$_y$=1/(f$_y$-g$_y$). The I$_o$ is the intensity of the x-ray beam incident on G$_1$ grating, and I'$_{1,2}$ is the average transmission" with --frequency $f' = 1/(T'_y \sin(atan(T'_x/T'_y)))$ with periods $T'_x = 1/(f_x - g_x)$ and $T'_y = 1/(f_y - g_y)$. The $I_0$ is the intensity of the x-ray beam incident on G$_1$ grating, and $\Gamma_{1,2}$ is the average transmission--

Signed and Sealed this  
Fifteenth Day of September, 2020

Andrei Iancu  
*Director of the United States Patent and Trademark Office*